United States Patent [19]

Hill

[11] Patent Number: 5,380,530
[45] Date of Patent: Jan. 10, 1995

[54] ORAL CARE COMPOSITION COATED GUM

[75] Inventor: Ira D. Hill, Locust, N.J.

[73] Assignee: WhiteHill Oral Technologies, Hazlet, N.J.

[21] Appl. No.: 996,939

[22] Filed: Dec. 29, 1992

[51] Int. Cl.⁶ .......................... A61K 9/68; A23G 3/30
[52] U.S. Cl. ...................................... 424/440; 424/48;
   424/439; 514/900; 514/902; 514/975
[58] Field of Search .................. 424/440, 48, 439, 441

[56] References Cited

U.S. PATENT DOCUMENTS

2,806,814  9/1957  Richter ................................. 167/93
4,609,543  9/1986  Morris et al. ....................... 424/440

OTHER PUBLICATIONS

L. Menaker, The Biologic Basis of Dental Caries, Chapter 5, Harper & Row (1980).
L. Menaker, The Biologic Basis of Dental Caries, Chapter 11, Harper & Row (1980).
L. Menaker, The Biologic Basis of Dental Caries, Chapter 12, Harper & Row (1980).
L. Menaker, The Biological Basis of Dental Caries, Chapter 14, Harper & Row (1980).
L. Menaker, The Biologic Basis of Dental Caries, Chapter 16, Harper & Row (1980).
L. Menaker, The Biologic Basis of Dental Caries, Chapter 18, Harper & Row (1980).
Topitsoglou et al., Caries Res., 17:369–378 (1983).
Segal et al., Journal of Pharmaceutical Sciences, vol. 74, No. 1, (1985).
Loesche et al., JADA, vol. 108, 597 (1984).
Makinen et al., JADA, vol. 111, 745, (1985).
Southard et al., JADA, vol. 108, 338 (1984).
Mordenti et al., Journal of Pharmaceutical Sciences, vol. 71, No. 12 (1982).
Fine et al., Journal of Clinical Periodontology, 12: 660–666 (1985).
Plaque, Current Approaches to Prevention and Control, JADA, vol. 109, Nov. 1984.
Winter et al., Caries. Res., 16:349–352 (1982).

*Primary Examiner*—G. S. Kishore
*Assistant Examiner*—James M. Spear
*Attorney, Agent, or Firm*—Ernest V. Linek

[57] ABSTRACT

Disclosed are several oral hygiene preparations including plaque disrupting and gingivitis control preparations in the form of chewing gums, wherein a chewing gum is coated with a plaque disrupting emulsion containing an ingestible surfactant and a polydimethyl siloxane emulsified therein, and wherein the emulsion coating can further contain a therapeutic substance such as the gingivitis control substance stannous fluoride.

17 Claims, No Drawings

ORAL CARE COMPOSITION COATED GUM

BACKGROUND OF THE INVENTION

The present invention relates to oral hygiene and specifically to the frequent interference with the formation of plaque and/or the control of gingivitis, hypersensitivity, etc., by regularly chewing a specially coated chewing gum. Plaque is a microbial coating on tooth surfaces, bound together by natural polymers, (mucopolysaccharides,) formed by microbial action on the cell debris, food remnants, sugars and starches in the mouth. Embedded in this polymer matrix are the bacteria normal to the oral cavity but, when trapped against tooth surfaces and protected by the matrix from easy removal, are in excellent position for "mischief." Most dental texts implicate plaque in the formation of caries, or tooth decay. In addition, these embedded bacteria release toxins that cause gingivitis, bleeding and swelling of the gums. Gingivitis can lead to periodontitis in which gums recede, pockets of infection form and teeth loosen.

Plaque formation is an ongoing process. Various gel and paste dentifrice preparations, mouth rinses, mouth prerinses and spray preparations make plaque and/or tartar control claims. One disadvantage of these toothpaste and rinse preparations is that only a relatively short time during which the teeth are being cleaned or the mouth is being rinsed is available for these preparations to take effect. These preparations generally have little residual effect on plaque formation. Additionally, some of these preparations such as mouth rinses and prerinses contain various antimicrobial substances which may alter the critically balanced microflora of the mouth. Another disadvantage of these toothpaste and rinse preparations is the general infrequency of use. That is, most are used once or perhaps twice daily and seldom when they are most needed, e.g., after meals, snacks, smoking, drinking, coffee breaks, etc. The present invention also relates to therapeutic oral hygiene preparations including preparations suitable for the control of gingivitis.

Effective oral hygiene requires that three control elements be maintained by the individual:

1. Physical removal of stains, plaque and tartar. This is accomplished in the strongest sense by scraping and abrasion in the dentist's office. Self administered procedures are required frequently between visits and range from tooth brushing with an appropriate abrasive toothpaste through flossing and water jet action down to certain abrasive foods and even the action of the tongue against tooth surfaces.
2. Suffactant Cleansing. This is required to remove food debris and staining substances before they adhere to the tooth surfaces as well as normal dead cellular (epithelial) material which is continually sloughed off from the surfaces of the oral cavity and microbial degradation products derived from all of the above. The ease of surfactant cleansing is enhanced if the surface of the tooth has a lower surface energy so that debris and plaque precursors cannot firmly adhere. Besides the obvious hygienic and health benefits related to simple cleanliness provided by surfactants, there is an important cosmetic and sense-of-well-being benefit provided by surfactant cleansing. Research has shown that the primary source of bad breath is the retention and subsequent degradation of dead cellular material sloughed off continuously by the normal, health mouth.
3. Frequency of Cleansing. This is perhaps the most difficult to provide in today's fast-paced work and social environment. Most people recognize that their teeth should be brushed at least 3 times a day plus after each snacking occasion.

The simple fact is that most of the population brush once a day, some brush morning and evening, but precious few carry toothbrush and dentifrice to use the other three or four times a day for optimal oral hygiene.

Consumer research suggests that the population brushes an average of 1.3 times a day. Thus, the 24 hour period between brushings for a majority of the population provides optimum plaque forming conditions with no interruptions.

Since plaque is regarded by most of the dental profession as a causative agent leading to various dental pathologies as noted above, there is considerable desire by most consumers to remove or prevent the formation of plaque on a daily basis. There are three oral care strategies which address the problem of plaque: abrasion, anti-microbial agents and removal of precursors to plaque.

1. Abrasive removal of the plaque film, once it has firmly adhered to the tooth surface, is the only totally effective cleansing mechanism. Again, professional dental hygiene is the most effective, but recently a number of special abrasive toothpastes have been accepted by dental organizations as partially removing adhered plaque and the tartar which subsequently forms from the plaque;
2. Antimicrobial action could affect plaque formation in two ways, (a) reducing the number of bacteria in the mouth which form the mucopolysaccharides and (b) killing those bacteria trapped in the film to prevent further growth and metabolism. However, the medical and dental community is divided about the advisability of frequent use of antimicrobial agents in the mouth in rinses or prerinses, especially the most effective ones, except under strict supervision of licensed practitioners. There are a number of reasons given, but one concern is that such materials would upset the ecological balance of the mouth. A balanced, "friendly" microbial population is necessary to prevent pathogenic organisms from taking over, and
3. Removal of plaque precursors requires the reduction of food sources and the building blocks required for the bacteria to synthesize the mucopolysaccharides which polymerize into plaque film. Going far back into the chain of events leading to plaque formation and interrupting the chain has much to commend it as a sound oral hygiene strategy. However, for this strategy to be effective, the plaque building blocks must be interrupted periodically. As noted above, hereto, the oral hygiene preparations described above fall short on "frequency-of-use" basis.

For reference, see, L. Menaker, The Biologic Basis of Dental Caries, Chapters 5, 11, 12, 14, 16 and 18, Harper & Row (1980).

Efforts have been made over the years to address the problem of dissolution or demineralization of tooth enamel and the resultant formation of dental caries. As is well known, dental plaque accumulates on the teeth as the result of the growth and metabolism of certain bacteria, such as *Streptococcus mutans*, which are nourished by cariogenic comestibles, particularly those containing sugars. Such bacteria are involved in the formation of dental plaque which accumulates as a deposit on the surfaces of teeth. The metabolism of bacteria within the plaque results in the generation of high levels of acids which are detrimental to the teeth and contribute to the production of dental caries.

Stannous fluoride, $SnF_2$, has been used in dentistry since the 1950's as a chemical adjunct to prevent dental caries. Topical applications of $SnF_2$ consistently have shown dramatic reductions in dental caries activity with minimal side effect. Evidence has also accumulated that $SnF_2$ has antibacterial properties which may affect its anticaries properties as well as inhibit plaque formation and gingivitis. See Tinanoff, "Review of the Antimicrobial Action of Stannous Fluoride," 1990.

Addy et al., 1988, reported a desensitizing effect for fresh $SnF_2$ due to a covering or obturation of tubules in hypersensitive dentine. There is also an indication that $SnF_2$ may be effective in controlling Candida sp. colonization of denture plaque. See Hill et al., U.S. Pat. Nos. 5,057,310; 5,098,711 and 5,165,913.

Prescription ($R_x$) nonaqueous gels of glycerine and $SnF_2$, such as Scherer Laboratory's, Gel-Kam are perhaps the most widely used form of $R_x$ $SnF_2$ available commercially. These gels are generally prescribed for the treatment of caries and hypersensitive teeth as well as gingivitis.

Unfortunately, in spite of its promising results, the effective use of $SnF_2$ has been drastically limited by its inherent instability in the presence of oxygen, water, abrasives, and the like.

In addition to the inherent instability of $SnF_2$, most $SnF_2$ products suffer from poor patient compliance, attributed in part to the nonaqueous carriers required to maintain activity, to the metallic taste of the product, as well as to the methods of application which usually include a brushing step separate and apart from the use of a dentifrice. For example, brush-on $SnF_2$ gels require the patient to brush at least four times/day, i.e., twice with the gel and twice with a regular dentifrice. Compliance in such a treatment regimen drops to about 30%, an unacceptable level, as documented by Hastrieter's review of Wolf et al.'s 1989 Gel-Kam study.

With the advent of fluoride in water and fluoridated dentifrices, gum disease, gingivitis, hypersensitive teeth, root caries in the elderly and Candida sp. disorders in denture wearers, have replaced caries in children as the dominant oral care concerns of the '90's requiring special treatment. For example, a recent NIH survey established that 90% of adults age 65 or older have some form of gum disease, and over 123 million adults in the U.S. suffer from gum disease. Moreover, one out of six adults suffer from hypersensitivity at one time or another, while ten million adults are chronic sufferers. Additionally, the millions of adults who undergo periodontal treatment, or have their teeth cleaned, can experience hypersensitivity discomfort ranging from an uncomfortable feeling to severe pain. Most denture wearers suffer from "denture breath" attributed in part to Candida sp. colonization of denture plaque and/or plaque-like coatings on dentures.

Recent reviews on dentine hypersensitivity have deduced that the transmission of pain stimuli across dentine is by a hydrodynamic mechanism. This is confirmed by the open tubules (microscopic openings) present in normal teeth). Various stimuli cause fluid movement in these tubules which activate nerve endings in the pulp.

Considerable evidence has accumulated in the past 20 years to show that topical applications of $SnF_2$ reduce S. mutans levels as well as demonstrate antiplaque properties. These antiplaque and antigingivitis benefits of $SnF_2$ appear to be related to frequent, i.e., several times/day treatment with $SnF_2$.

Root caries is attributed to the recession of gums and is a common condition in the elderly. Candida sp. yeast disorders are estimated to occur in approximately 90% of denture wearers. These disorders lead to, or are associated with, stomatitis and thrush (candidiasis).

There is therefore a definite need in the art for oral hygiene preparations containing microbially active $SnF_2$ that retain the desired antibacterial activity over the use life of the preparations. There is also a need in the art for oral hygiene preparations containing microbially active $SnF_2$ that are pleasant to use, encourage compliance and support frequent usage throughout the day. There is a further need in the art for new methods of treating caries, coronal caries, gingivitis, plaque buildup, hypersensitivity and Candida sp. infections of denture plaque with microbially active $SnF_2$ products in various forms.

There is a further need in the art for delivery vehicles for microbially active $SnF_2$ which achieve rapid transport of $SnF_2$ into fissures, crevices in dentures and other prosthesis where the microbial activity of $SnF_2$ can be employed to fight plaque and disrupt the colonization of denture plaque by yeast type organisms while protecting the $SnF_2$ from degradation of its microbial activity.

In view of the foregoing it is an object of this invention to provide an oral hygiene preparation that disrupts plaque formation with or without providing various therapeutic substances to the oral cavity such as $SnF_2$ for treating caries, gingivitis, hypersensitivity and Candida sp. infections.

It is also an object of this invention to provide an oral hygiene preparation containing various therapeutic substances including microbially active $SnF_2$ that are pleasant to use, encourages compliance and repetitive usage.

It is a further object of this invention to provide an effective method for treating caries, gingivitis, hypersensitivity, plaque buildup and Candida sp. infections.

It is yet another object of this invention to provide a method of manufacturing oral hygiene preparations for fighting plaque as well as preparations containing a microbially active form of $SnF_2$.

Chewing gum has over the years been advocated as a possible excellent adjunct for cleaning the teeth because people find the chewing of gum very pleasurable and chew gum more frequently for much longer periods of time than they brush their teeth. Chewing gum is especially advantageous for use in circumstances where tooth brushing is not possible or convenient, such as after lunch, while traveling, or while working.

Chewing gum stimulates saliva because of the chewing action, flavors and sweetness. In the first few minutes of chewing, studies have shown a ten-fold increased in salivary flow. After the flavor and sweeteners are extracted, there is still a three-fold increase in saliva flow. This saliva stimulation after eating has a number of benefits. For example, stimulating saliva after eating helps:

dilute and clear food debris and fermentable carbohydrates from the mouth, deliver buffers such as bicarbonate, proteins, urea, to the plaque, neutralize plaque acid due to buffering action and dilution, inhibit mineral loss due to shorter time of acid exposure, and promote enamel, remineralization due to higher pH and the enamel protective effects of calcium, phosphate and fluoride.

Most eating occasions lead to prolonged acid production. Dentists advise snacking in moderation, brushing teeth twice daily with a fluoride toothpaste, and cleaning teeth soon after eating. However, since tooth brushing with toothpaste after eating is often impractical and inconvenient, the use of a salivary stimulant can reduce acid production and facilitate a returning to a near neutral pH conductive to remineralization. Two recent papers by Dr. S. L. Creanor, et al., in Glasgow and Drs. R. H. Manning and W. M. Edgar in Liverpool on remineralization illustrates the importance of stimulating saliva after eating in a fluoride environment, e.g., Caries Res. (26.3.92 No. 22, Page 215 and J. Clin. Dent., Vol. III No. 3, respectively.

As is well known, salivation is an important physiological function which has several benefits in addition to those relating to digestion.

One of those benefits is the washing of tooth enamel surfaces and their surrounding soft tissues or game. This washing provides a preventive effect against disease in direct relation to the rate of salivary flow from the four major salivary glands which empty into the human mouth under various stimulations.

Chewing gum not only provides the flavor and chewing factors for saliva stimulation but also achieves mechanical dental cleansing, making it an ideal and natural mechanism for promoting dental health.

The use of chewing gums to deliver various substances into the oral cavity is extensively described by the prior art. Generally, these references teach incorporating various substances into the gum mix during the processing of the gum. The substances incorporated in the gum base are then released from the gum during masticating. For example;

A. Some prior art methods have been disclosed for the incorporation of active or insoluble ingredients into sugar containing gum bases, U.S. Pat. No. 3,075,884 teaches a method for obtaining the release of solid active ingredients from a gum base by dispersing the solid active ingredient throughout the corn syrup ingredient of the gum prior to the admixture of the corn syrup with the gum base; U.S. Pat. No. 3,011,919 teaches a method for incorporating active ingredients, including phosphates, into slab chewing gum, by coating the active ingredients with wet sugar;

B. U.S. Pat. No. 3,352,689 does disclose the formulation of a sugarless gum prepared from gum base, gum acacia-in-water, gum acacia powder, sorbitol, mannitol, sweeteners and flavoring agents, which may contain additional active ingredients such as phosphates; however, no statement is made concerning the form in which these active ingredients must be or the manner for incorporating these active ingredients into the sugarless gum formulation so as to insure the release of effective amounts of the active ingredients into the oral cavity. See also U.S. Pat. No. 3,655,866;

C. It is also well known in the art that mineral adjuvants such as calcium carbonate are added to chewing gum compositions to act as fillers or to provide non-stick properties. Thus, for example, U.S. Pat. No. 4,357,355, to E. Koch et al., discloses a non-stick bubble gum base composition that contains about 5% to about 25% by weight of calcium carbonate;

D. A number of chewing gum compositions have been disclosed in the art which are said to inhibit or reduce plaque in the oral cavity. For example, U.S. Pat. Nos. 4,148,872, 4,150,112, 4,156,715, 4,156,716, 4,157,385, 4,159,315, 4,160,054, 4,160,820, 4,161,517, and 4,170,632, all to A. Wagenknecht et al., disclose chewing gum compositions effective in inhibiting or reducing plaque in the oral cavity. These chewing gum compositions contain a chewing gum base and a surface active agent, and, in some instances, a zinc compound or a plaque inhibiting flavor. In addition, a calcium carbonate abrasive may be included in the aforementioned chewing gum compositions. See also, U.S. Pat. Nos. 3,974,293, 3,984,574; 3,651,206; 4,568,537; 4,474,749 and 4,828,820. U.S. Pat. No. 4,029,760 discloses pharmaceutical chewing gums for the treatment of gingivitis containing at least one carrageenin;

E. U.S. Pat. No. 4,400,372, to J. C. Muller et al., discloses a chewing gum composition containing a chewing gum base, at least one non-toxic source of an acid and calcined kaolin particles having a median diameter of 2 micrometers of less, wherein substantially all of the kaolin particles are less than 20 micrometers in diameter;

F. U.S. Pat. No. 3,590,120, to J. C. Muller, discloses a chewing gum composition containing an insoluble gum base; zirconium silicate particles as a cleaning and polishing agent, wherein at least 20% by weight of said particles are up to about 3 microns in size and between 5% and 40% by weight are about 10 to about 20 microns in size; and a dental plaque removing agent which may be sodium carbonate, sodium bicarbonate, or chloroform. See also U.S. Pat. Nos. 3,255,018 and 3,651,206; and G. The use of cationic antimicrobial agents to reduce plaque and gingivitis has been recognized for many years wherein these antimicrobial compositions are included in the chewing gum base. Included among references disclosing, such compositions are U.S. Pat. Nos. 3,937,805, Feb. 10, 1976 to Harrison; 3,937,807, Feb. 10, 1976 to Haefele; 4,080,441, Mar. 21, 1978 to Gaffar et al.; 4,241,049, Dec. 23, 1980 to Colodney et al.; 3,925,543, Dec. 9, 1975 to Donohue; 4,256,731, Mar. 17, 1981 to Curtis et al.; 4,217,342, Aug. 12, 1980 to Gaffar; 4,259,316, Mar. 31, 1981 to Nakashima et al.; 4,039,409, Jan. 4, 1982 to CollPalagos et al.; and U.S. Pat. No. 4,169,885, Oct. 2, 1979 to Raaf et al.

The "Effect of Chewing Gums Containing Xylitol, Sorbitol or a Mixture of Xylitol and Sorbitol on Plaque Formation, Ph Changes and Acid Production in Human Dental Plaque": is published in Carles Res., 17: 369–378 (1983).

Historically, researchers in gum have focused on incorporating various substances from flavors to plaque fighting substances into the gum base, or gum base adjuncts for controlled released during chewing. For example:

A. Yolles, in U.S. Pat. No. 3,818,107 issued Jun. 18, 1974, describes chewing gums which incorporate the flavor in a polymeric backbone. Yolles states that the flavor release in the chewing gum is sustained by the molecular arrangement of the flavor group. In U.S. Pat. No. 3,651,206 issued to Litchfield et al., on Mar. 21, 1872, are described chewing gums containing various aliphatic aldehydes as anticaries agents. Various oral preparations for preventing dental plaque are described in U.S. Pat. No. 3,940,476 issued Feb. 24, 1976 to Hass. Comollo states in U.S. Pat. No. 3,984,574 issued Oct. 5, 1976 that non-tacky chewing gums may be made containing mono- and diglycerides of fatty acids in an amount up to ten percent (10%) by weight of the base composition;

B. Clark, in U.S. Pat. No. 3,930,026 issued Dec. 30, 1975, describes the enhancement of flavor in chewing gums obtained by sorbing the flavoring onto a hydrophilic colloid in conjunction with a surfactant. Among the surfactants disclosed are anionic materials, including sodium di(2-ethylhexyl)sulfosuccinate. Clark also states that nonionic surfactants may be used to sorb the flavor into the gum including fatty acid monoglycerides or fatty acid diglycerides;

British Pat. No. 1,296,952 reported by Cancro et al. and published Nov. 22, 1972 states that plaque and calculus may be diminished by zinc phenolsulphonate and certain enzymes in dentifrice compositions. The Cancro patent also describes the use of certain abrasives, buffering agents, and various surfactants. British Pat. No. 1,372,932 published Nov. 6, 1974, describes purported anticaries compositions including chewing gums, dentifrices and candy-like products. In particular, the aforementioned British patent states that stearol-2-lactylate has been found effective to inhibit the production of dextran in the mouth;

C. U.S. Pat. No. 3,821,417 issued to Westall et al. on Jun. 28, 1974, describes the use of dihydrochalcone in chewing gums. This patent further describes the use of butylated hydroxyanisole, butylated hydroxytoluene and propyl gallate as antioxidants in chewing gums. Duross, in U.S. Pat. No. 3,973,041 issued Aug. 3, 1976 describes the use of sorbitol powder, butylated hydroxyanisole, and glycerine in chewing gums. Additional disclosures of sorbitol as well as other sugars, such as xylitol, are made in various United States Patents including: U.S. Pat. No. 4,000,320 issued to Klose et al., on Dec. 28, 1976; U.S. Pat. No. 3,899,593 issued to Hammond et al., on Aug. 12, 1975; U.S. Pat. No. 3,914,434 issued Oct. 21, 1975 to Bohni; U.S. Pat. No. 3,296,079 issued Jan. 3, 1967 to Griffin; and U.S. Pat. No. 3,655,866 issued Apr. 11, 1972 to Billoti; and D. Various additives for chewing gums have been suggested to reduce or eliminate the problem of chewing gum adhering to dentures and artificial teeth, such as lecithin as disclosed in U.S. Pat. No. 2,197,719, lanolin as disclosed in U.S. Pat. No. 2,197,718 and silicone oils as disclosed in U.S. Pat. No. 2,761,782. U.S. Pat. No. 3,255,018 to Comollo discloses the use of water-soluble hydrolyzable tannin, such as tannic acid or polymer-tannic acid edicts, in combination with type A or B gelatin water-containing hydrophilic polymer gels. See also U.S. Pat. Nos. 2,273,425; 2,383,145; 2,429,664; 3,285,450; 3,440,060 and 3,984,574.

The general disclosure of nonionic surfactants for use in oral products is also well discussed in the prior art, particularly with reference to dentifrices and rinses. For example:

A. Tomlinson in U.S. Pat. No. 4,130,636 discloses dental creams and mouthwash compositions free from bitter surfactant taste wherein the surfactant is an alkyl polyglycol ether carboxylate. A mouthwash having superior taste characteristics and improved clarity is disclosed by Januszewski in U.S. Pat. No. 3,639,563. The improved clarity is obtained by selecting nonionic surface active agents for their ability to solubilize one or more oily components contained in the mouthwash. Thus, polyoxypropylene-polyoxyethylene block polymers and polyoxyethylene derivatives of sorbitan esters are disclosed as useful surfactants which solubilize certain oily components and thus provide improved clarity in the mouthwash;

Pensak et al., in U.S. Pat. No. 3,947,570, also disclose a visually clear, haze-free mouthwash free from unpleasant taste which includes a nonionic surfactant which is a polyoxyethylene derivative of a sorbitan ester;

B. Jackson et al., in U.S. Pat. No. 2,677,700, disclose polyoxyalkylene surface-active block polymers, Example 6 thereof disclosing a propoxylated cetyl alcohol. There is an indication, in Column 24, that the surface active agents disclosed would have freedom from the usual bitter taste generally associated with nonionic suffactants of the prior art, and C. Schmolka, U.S. Pat. No. 4,465,661 discloses various Pluronic-type, nonionic surfactants suitable for use in various oral care products.

Hill et al., U.S. Pat. Nos. 4,950,479 and 5,057,309 disclose the claimed emulsions of the present invention in "liquid center chewing gums". However, there is no teaching or suggestion that the Hill et al. emulsions can be coated onto chewing gum and subsequently released into the oral cavity at a predetermined plaque disrupting level and rate.

One of the leading researchers in gum technology, the Wm. Wrigley Jr. Company, has contributed various innovations to chewing gum technology, including:

a. the addition of lanolin and lecithin to chewing gum mixes to decrease tackiness and reduce cohesive properties, U.S. Pat. Nos. 2,197,718 and 2,197,719 respectively;

b. the addition of certain paraffin waxes to chewing gum mixes imparts smoothness and freedom from tack, U.S. Pat. No. 2,137,746;

c. chewing gum compositions possessing anticaries activity based on the addition of various aldehydic compounds to the gum base, U.S. Pat. No. 3,651,206;

d. abhesive chewing gum compositions, U.S. Pat. No. 3,984,574, and e. a method of preventing tooth remineralization, U.S. Pat. No. 4,568,537.

The release of active ingredients from the gum base is a major problem and one which has confronted the industry for a long time despite the fact that slab chewing gums on a weight basis are more than 75% water soluble materials such as sugars, sugar substitutes, corn syrup, and the like.

It therefore has been the usual practice in the industry when manufacturing chewing gums having active ingredients to deposit the active ingredient upon the exterior of a gum nugget or center, usually with an underlying thin layer of hard sugar. The outer layer of hard sugar is generally produced by tumbling the units in coating pans into which saturated solutions of sugar are poured and the water driven out by aeration, the finished piece being commonly called "candy coated gum". The use of candy coated gum allows for the dissolution of the active ingredient in the mouth before it is chewed into the gum base. See U.S. Pat. Nos. 3,075,884 and 3,011,949. This method of production is costly and eliminates desired slab forms of gum containing such an active ingredient. See also U.S. Pat. Nos. 1,629,461, 1,771,982 and 2,198,165.

SUMMARY OF THE INVENTION

It has now been found that chewing gums provided with a special coating as set forth herein, can provide inter alia, the following beneficial effects to the user; plaque disruption, gingivitis control, hypersensitivity treatment, stomatitis treatment, and the like. The chewing gums of the present invention are coated with an emulsion containing an ingestible surfactant and a polydimethyl siloxane emulsified therein. If desired, the emulsion coating can contain various therapeutic substances such as microbially active stannous fluoride, and the like.

One embodiment of the present invention combines two of the three primary elements of oral hygiene, namely surfactant-emulsifier cleansing and reduction of the surface energy required for plaque adherence by coating the tooth and oral tissue surfaces with the polydimethyl siloxane emulsified therein coupled with frequent cleansing to achieve plaque disruption. The unexpected plaque disrupting effect of the emulsion coated chewing gums of the present invention are obtained without antimicrobial ingredients and without altering the critically balanced microflora of the oral cavity.

A second embodiment of the present invention comprises the innovative coating processes used to lay down on the surface of the chewing gums the melt emulsions of the invention, wherein the melt emulsion coating substantially releases from the chewing gum into the oral cavity, shortly after chewing starts at a predetermined rate and in a predetermined amount.

A third embodiment of the invention comprises therapeutic chewing gums characterized by an emulsion coating as described earlier, wherein the emulsion coating contains a therapeutic substance such as stannous fluoride and the emulsion coating-therapeutic substance mixture is released into the oral cavity from the gum, during chewing, at a predetermined rate and in a predetermined amount. Other therapeutic substances include: oral care medicaments such as chlorhexidine, triclosan, potassium nitrate, various quaternaries, the active essential oils in Listerine ®, and the like, various antibiotics, analgesics, oral discomfort relief active ingredients, and the like.

A fourth embodiment of the present invention comprises the methods of treating the oral cavity by chewing various emulsion coated gums and releasing various plaque disrupting and other therapeutic substances into the oral cavity from said gums at a predetermined rate and in a predetermined amount.

DETAILED DESCRIPTION OF THE PREFERRED EMBODIMENT

The present invention comprises: a chewing gum coated with an emulsion of an ingestible surfactant or emulsifier and a polydimethyl siloxane insoluble in said surfactant or emulsifier, wherein the coating releases from the gum into the oral cavity during chewing, at an effective predetermined rate and in an effective predetermined amount.

Suitable surfactants and emulsifiers for use in the present emulsion coating for gum include:
sodium lauryl sulfate,
sodium lauroyl sarcosinate,
polyethyleneglycol stearate,
polyethyleneglycol monostearate,
coconut monoglyceride sulfonates,
soap powders,
sodium alkyl sulfates,
sodium alkyl sulfoacetates,
alkyl polyglycol ether carboxylates such as those described in U.S. Pat. No. 4,130,636,
polyoxyethylene derivatives of sorbitan esters, such as those described in U.S. Pat. Nos. 3,639,563 and 3,947,570,
propoxylated cetyl alcohols, such as those described in U.S. Pat. No. 2,677,700.

Particularly preferred surfactants include block copolymers comprising a congeneric mixture of conjugated polyoxybutylene and polyoxyethylene 1200 compounds having as a hydrophobe, a polyoxybutylene polymer of at least molecular weight; such as those described in U.S. Pat. Nos. 4,343,785, 4,465,663, 4,511,563 and 4,476,107.

These polymers are prepared by adding the required number of mols of propylene oxide to the two hydroxyl groups of propylene oxide to the two hydroxyl groups of propylene glycol to form a hydrophobic base and then adding ethylene oxide to both ends of the hydrophobic base to form hydrophilic polyoxyethylene groups of controlled length. Various species of such polymers, including those defined above as useful in the invention, are available commercially from Wyandotte Chemicals Corporation of Wyandotte, Mich. under the trademark "Pluronic."

Especially preferred are the commercially available surfactants which include the polyoxyethylene-polyoxybutylene block copolymers such as Pluronic F108, and F 127 (BASF) and polysorbates such as Tween 40, and 80, (Hercules.)

Suitable emulsifiers for use in the present emulsion coating include various polyethylene glycols commonly referred to as PEG and PEG oleate, PEG Beeswax, mono-methylether polyethylene glycol, and the like.

The polydimethyl siloxanes suitable for use in the chewing gum coatings of the present invention can be characterized as follows, they:
(1) suppress the tendency of the surfactant cleaners present to foam;
(2) are safely ingestible at the concentrations used;
(3) have an affinity for mouth and teeth surfaces;
(4) are neutral, inert and do not support biological activity;
(5) modify the surface energy properties of surfaces of the mouth such that it is more difficult for food particles, cellular debris and various plaque precursors and formers to attach to these surfaces;

(6) form a thin, transparent coating that does not build up on mouth surfaces and is removed by the normal clearing and flushing action of the mouth;

(7) impart a pleasant "smooth" feeling to the surfaces of the mouth and teeth, and (8) are insoluble in the surfactant or emulsifiers used herein.

These polydimethyl siloxanes are commonly referred to as dimethicone or simethicone (when admixed with small amounts of silica) are commercially available from Dow Corning Corp., Midland, Mich. and other suppliers, in both food and medical grades. Polydimethyl siloxanes are water-white, viscous oil-like liquids. See Merck Index, 11th Edition, Monograph Number 8486 and R. R. McGregor's text "Silicones and Their Uses", McGraw-Hill (1954). See also, U.S. Pat. Nos. 2,441,098; 2,606,510 and 2,761,782.

Polydimethyl siloxanes suitable for the emulsion coatings of the present invention can be described by the general structure:

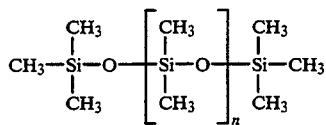

wherein n represents the number of repeating dimethyl siloxane units and can range from below 100 to several thousand. Typically, the molecular weight of these polydimethyl siloxanes are designated by their viscosity. Safety, efficacy and processing considerations suggest that viscosities from about 350 centistokes to 12,500 centistokes are preferred for the present invention.

Examples of various surfactant or emulsifier-polydimethyl siloxane emulsions suitable for coating various chewing gums of the present invention are described in Table 1 below.

TABLE I

ILLUSTRATIVE EXAMPLES OF MICRODENT COATING MIXTURES
(Percent by Weight)

| Example | Surfactant | polydimethyl siloxane | sorbitol powder | sweeteners | flavor | mouthfeel agent | % by wt coated on gum |
|---|---|---|---|---|---|---|---|
| 1 | (1)F-127 80.0 | (3)DC 360 @ 350 cs 20.0 | none | none | none | none | 1.5 |
| 2 | F-127 56.7 | DC 360 @ 1000 cs 20.0 | 20.0 | saccharin 0.1 | peppermint 0.2 | carrageenan 3.0 | 2.1 |
| 3 | F-127 30.0 | DC 360 @ 12,500 cs 30.0 | 30.0 | aspartame 0.2 | Doublemint 0.4 | none | 3.0 |
| 4 | (2)F-108 20.0 | (4)Antifoam 1500 30.0 | none | none | none | (5)Klucel MF 2.0 | 3.8 |
| 5 | F-108 20.0 | DC 360 @ 12,500 cs 20.0 | 59.8 | aspartame 0.1 | none | none | 1.8 |
| 6 | PEG 150 62.5 | DC 360 @ 350 cs 20.0 | 32.0 | none | spearmint 0.1 | (6)Methocel K4M 2.7 | 4.3 |
| 7 | PEG 100 40.0 | DC 360 @ 12,500 cs 4.4 | 15.0 | saccharin 0.2 | IFF van-mint 0.3 kaolin 25.3 | carrageenan 15.0 | 5.6 |
| 8 | PEG 150-OLEATE 70.0 | DC 360 @ 1000 cs 14.0 | 10.0 | aspartame 0.2 | IFF van-mint 0.2 | Klucel MF 5.6 | 2.1 |
| 9 | PEG 20-BEESWAX 39.5 F-108 30.0 | DC 360 @ 1000 cs 15.0 DC 360 @ 12,500 cs 15.0 | none | saccharin 0.3 | IFF tutti-frutti 0.3 | none | 2.8 |

(1)Pluronic F-127(BASF) brand of poloxamer 407
(2)Pluronic F-108 (BASF) brand of poloxamer 338
(3)Dow Corning Medial Fluid 360 in various viscosity (cs) grades
(4)Dow Corning Food Antifoam 1500
(5)Ethyl propyl cellulose (Aqualon)
(6)Carboxy methyl cellulose (Dow)

The concentration of the emulsion as a percent by weight of the gum to which it is applied can range from between about 0.5% by weight and about 6% by weight. Preferably the coating comprises from between about 1.0% and about 4.0% by weight of the gum. On an absolute weight basis, the coating may be applied in a range from between about 10 mg/piece to about 150 mg/piece. Preferably the coating can weigh from between 20 mg/piece and 100 mg/piece.

The chewing gum coated with the surfactant-emulsifier-polydimethyl siloxane emulsion is a typical chewing gum composition manufactured by utilizing conventional chewing gum manufacturing operations to which the innovative coating processes of the present invention are applied.

All manner of natural or synthetic gum bases are to be considered as included within the scope of the present invention. Examples of suitable gum bases include chicle, gutta percha, jelutong, balata, namaquland rubber, almeidana gum, abba rubber, gutta siak, gutta cotie, gutta kay, gutta hangkang, gutta penang, and yellow gutta. Further examples of gum bases include rosins, such as comarone resin, pontianak resin, copal gum, kauri gum, dammar gum, sweet bay gum, spruce gum, and balsams. Moreover, suitable gum bases include crown gum, nisperio, rosidinha, pendare, perillo, niger gutta, and tuno.

Additional chewing gum base materials include elastomers such as polyisobutylene, polyisoprene, isobutyleneisoprene copolymers and copolymers of butadiene and styrene, hydrogenated or partially hydrogenated vegetable oils such as soy bean, cotton seed, corn, peanut, and palm or animal fats such as tallow and lard. In addition paraffin, beeswax, petroleum wax, polyethylenes, and polyvinylacetates may be employed. Further descriptions of suitable chewing gum bases are found in U.S. Pat. No. 2,366,589 issued to Borglin Jan. 2, 1945; U.S. Pat. No. 3,821,417, issued to Westall, et al. on Jun. 28, 1974; U.S. Pat. No. 4,041,179 issued to Stubits et al. on Aug. 9, 1977; U.S. Pat. No. 3,984,574 issued to Comollo on Oct. 5, 1976 and U.S. Pat. Nos. 1,807,704 and 2,076,112 all of which are hereby incorporated herein by reference.

Further descriptions of suitable chewing gum bases are found in U.S. Pat. No. 4,357,355, to E. Koch et al., U.S. Pat. No. 4,387,108, to E. Koch et al., and U.S. Pat. No. 4,518,615, to S. R. Cherukuri et al., all of which are hereby incorporated herein by reference.

The gum base referred to above covers the nonnutritive, masticatory substance in chewing gun, as defined in the Federal Food, Drug and Cosmetic Act. In the regulation covering chewing gum ingredients under the Food Additives Amendment (Federal Register, p. 4419, May 9, 1962), paragraph (a) sets forth the ingredients permitted in chewing gum base under the regulation, and paragraph (c) defines the term "chewing gum base" as non-nutritive masticatory substance comprised of one or more of the ingredients named and so defined in paragraph (a) of this section. Suitable representative chewing gum bases which can be employed with facility in formulating the chewing gum compositions of the invention are those disclosed, for example, in U.S. Pat. No. 2,284,804 of F. T. De Angelis and U.S. Pat. No. 2,137,746 of R. L. Wilson, U.S. Pat. No. 2,383,145 of J. E. Moose, U.S. 2,288,100 of G. J. Manson and U.S. Pat. Nos. 2,366,589; 3,821,417; 4,041,179 and 3,984,574, all of which are hereby incorporated herein by reference.

The coated chewing gum products of the present invention are pleasant to use. The various flavors in the emulsion coatings of the present invention are formulated to be as pleasant as a good quality chewing gum and to contribute this pleasant taste over a longer-than-expected time period thus enhancing the "its working" perception without negative medicinal connotations which are found to reduce frequency of use and undermine the frequent cleansing advantage of previous therapeutic chewing gums. The feeling in the mouth is equally pleasant. A smooth, "some-thing's happening" feeling is perceived immediately upon the start of chewing, followed by a clean, fresh, well lubricated mouth and tooth surface which unexpectedly persists much longer than traditional uncoated chewing gums.

The combination of certain surfactants and/or emulsifiers with certain polydimethyl siloxanes wherein the latter is inherently insoluble in the former, in a coating on a chewing gum is novel. The plaque disrupting results obtained with chewing gum containing this coating is novel. Furthermore, the surfactant-polydimethyl siloxane-saliva mixture obtained in the mouth is ingestible and can be pleasantly swallowed, which further distinguishes this plaque fighting gum from typical plaque fighting products such as dentifrices used with a toothbrush and most rinses and prerinses. For example, unlike typical surfactants used in dentifrice pastes, the surfactants of the present invention do not fill the mouth with foam and can be pleasantly swallowed which is necessary for the high frequency cleaning feature of the coated chewing gums of the present invention.

Surprisingly, the surfactant and/or emulsifier polydimethyl siloxane combination of the present invention retains good surface active properties and is able to clear the mouth of some cell debris, food debris, material alba, sugars, starches and other precursors to plaque. This surfactant-emulsifier cleaning from the coating chewing gums of the present invention is obtained with minimal foaming while simultaneously coating the surfaces of the oral cavity with a thin neutral film containing the plaque disrupting active ingredients of the composition. This neutral film is not metabolizable by resident oral cavity microorganisms. By contrast, natural film formers such as lecithin-containing substances and fats are known to form anti-attachment films on mouth surfaces but these films are not suitable for the purposes of the present invention since they are metabolizable and are not neutral. Most of these naturally occurring coating substances support biological activity rather than form non-supportive inert films and as such, work opposite of the suitable film formers of the present invention. See for example; Menaker, The Biologic Basis of Dental Caries, Chapter 16; Gibbons and Hoote, Ann. Rev. of Microbiol., 29 pp. 19–44; and Hayes, J. Dent. Res., 632, pp. 2–5 (1984).

As long as this transient inert coating in the oral cavity obtained from the coated chewing gums of the present invention remains, it:
1. restricts the subsequent adherence of plaque forming materials to the teeth, thus continuing the disruption of plaque formation;
2. continues to impart a "smooth" feeling to the mouth, prolongs the flavor perception of the coated chewing gums of the present invention, and
4. reduces the "fatigue" and "tired of chewing gum" factor, allowing for longer pleasure and contact time for various therapeutic substances which may be included in the coating.

Most users of the coated chewing gums of the present invention perceive a quite different feeling in the mouth than is perceived with typical chewing gums. For example,
1. the mouth feels exceptionally clean and smooth and the surfaces of the teeth are slick and shiny. This well lubricated feeling of the mouth is particularly beneficial to mouth breathers and those afflicted with mouth dryness;
2. the prolonged flavor perception is generally described as "freshness": and persists much longer with the compositions of the present invention than when the same flavor is introduced into the mouth in the form of a conventional uncoated chewing gum. This residual flavor benefit is an important element contributing to frequency of use, and
3. prior to swallowing the surfactant-polydimethyl siloxane coating, saliva mixture that is released during chewing of the gum, the user perceives that the combination is "doing something" in the mouth. This perceived signal of efficacy reenforces repeat usage and often motivates the user to a more frequent use pattern, a key element in maximizing the efficacy of the present invention. This increased frequency of use is perceived as a major advance in oral care compliance and should be welcomed by most oral care professionals.

Combining the various cleaning-coating-mouth-feeling benefits of the surfactant-polydimethyl siloxane emulsions compositions of the invention with a chewing gum, provides for the first time, a commercializeable product whose form of delivery works in conjunction with the product to be dispensed to promote frequent use i.e. frequent cleansing and plaque fighting. As noted above, infrequent cleansing remains as the major road block to effective oral hygiene. Effective but socially inconvenient toothpaste, mouth rinses, and prerinses are simply not used with the frequency required to obtain optimum interruption of plaque formation.

Frequency of cleansing is encouraged by the two unique characteristics of the coated chewing gums of the present invention. These cause the user to return to the invention frequently throughout the day, stimulated as much by enjoyment, as by conscious recall of "my mouth needs cleaning" after events such as meals, snacks, coffee breaks, drinks, smokes, and the like.

The therapeutic chewing gums of the present invention are characterized by an emulsion coating as described earlier, wherein the emulsion coating contains one or more therapeutic substances. At the outset of chewing the coated gum, the coating-therapeutic substance(s) mixture is released from the surface of the chewing gum into the oral cavity at a controlled rate and in a predetermined amount.

Therapeutic substances suitable for use in the emulsion coated chewing gums of the present invention include:
various antimicrobials,
microbially active stannous fluoride,
chlorhexidine,
triclosan,
various zinc compounds, including zinc chloride,
cationic antimicrobial agents including various quaternaries such
as cetylpyridinium chloride,
the essential oils in Listerine ®,
stearoyl-2-1-actate,
antioxidants including various aldehydic compounds as well as
propyl gallate,
various enzymes,
various antibiotics including tetracycline,
metronidazole,
strontium chloride,
potassium nitrate,
carrageenan,
cough and cold remedies, and the like.

Other substances which may also be included in the chewing gum base mixture and which may also be added to the emulsion coating include: non toxic sources for acid such as adipic acid in combination with calcined kaolin, calcium carbonate, sodium carbonate, sodium bicarbonate, various phosphates, dicalcium phosphate, tetra sodium pyrophosphate, lecithin, lanolin, hydrolyzable tannin, silica, and the like.

The various therapeutic additives which can be included in the emulsion coatings of the present invention have traditionally been used to treat various oral care conditions as well as other health concerns. For example, microbially active stannous fluoride is a well known for treating gingivitis, hypersensitivity and stomatitis. See Hill et al., U.S. Pat. Nos. 5,057,310; 5,098,711 and 5,165,913.

The relatively fast rate of release from the coated chewing gum of the emulsion coating-microbially active stannous fluoride mixture into the oral cavity would be an effective means for introducing controlled and efficacious levels of the microbially active stannous ion into the oral cavity. The pleasant tasting chewing gum encourages compliance and accordingly repetitive treatments throughout the day can be expected; thereby accommodating the fairly limited substantivity of the antimicrobial moiety, the stannous ion, to the oral mucosa.

Various emulsion coating compositions of the present invention containing various therapeutic substances and suitable for coating the chewing gums of the present invention are described in Table II below along with the oral condition to be treated.

TABLE II

THERAPEUTIC CHEWING GUMS
Type of Therapeutic Substance Added to Emulsion Coating (% by weight)

| EXAMPLE | Coating Mixture From Table I (qs to 100%) | Abrasive for cleaning and tartar control | Antimicrobial | Antibiotic | Dry Mouth | Oral Dicomfort |
|---|---|---|---|---|---|---|
| 10. | #1 | silica dentifrice grade (10–30) | | | | |
| 11 | #3 | | stannous fluoride (1.2–4.0) | | | |
| 12 | #4 | | | | Mineral salts (saliva equiv.) sodium fluoride (2 ppm - final) | |
| 13 | #5 | | | tetracycline (0.5–2.5) | | |
| 14 | #6 | | | | | benzocaine (4.0–10.0) |
| 15 | #5 | | | | | potassium nitrate (5.0) |
| 16 | #3 | | | | | pectin (5.0–15.0) |
| 17 | #8 | | triclosan (0.2–1.0) | | | |
| 18 | #9 | Kaolin (10–30) | | | | | mineral salts,
remineralization substances,
pectin,
benzocaine,
analgesics, for mouth & throat discomfort,
sanguinarine extract, The coating compositions of the invention may also contain certain phosphate salts, such as tetrasodium or tetrapotassium pyrophosphate(s), which have been shown to aid in the control of plaque and the calcified plaque called tartar.

The high flavor levels which can be pleasantly incorporated into emulsion coatings of this invention, whose frequent application is encouraged by the unique character of the invention, and which are retained in the mouth for surprisingly long time periods also contribute to the plaque controlling properties of this invention. For example, natural and synthetic flavor and sweetener agents as diverse as menthol, xylitol and glycyrrhizin are known to be beneficial towards plaque control and are included in the emulsion coating compositions of this invention (see, e.g., Segal, J. Pharm. Sci., 74 pp. 79–81 (1985) and Makkinen, J. Am. Dent. Assoc. III, pp. 740–741).

In addition to the coating compositions described above, preferred embodiments of the coatings use various viscosity control agents to impart certain viscosity characteristics to the coatings of the invention. It is believed that in these preferred embodiments of the invention, viscosity plays a role in achieving optimum mouth feel and flavor retention characteristics of the invention.

The conventional flavoring components suitable for the emulsion coatings of the present invention are exemplified by the following materials, menthol, anise oil, benzaldehyde, bitter almond oil, camphor, cedar leaf oil, cinnamic aldehyde, cinnamon oil, citronella oil, clove oil, eucalyptol, heliotropin, lavender oil, mustard oil, peppermint oil, phenyl salicylate, pine oil, pine needle oil, rosemary oil, phenyl salicylate, pine oil, thyme oil, thymol, wintergreen oil, lemon and orange oils, vanillin, and other flavoring oils generally regarded as safe (GRAS) by health authorities.

Additional adjutants can be added to the emulsion coatings to provide color, flavor, or sweetening effects, as desired. Examples of suitable sweetening agents include sorbitol, sodium cyclamate, saccharine, commercial materials such as Nutrasweet ® brand of aspartame and xylitol. If desired, the coloring agent is typically added in an amount of 0.01 percent to about 0.02 percent by weight. Citric acid is often utilized as a flavor additive. All types of flavoring materials are generally used in amounts of about 0.01 to about 5.0 percent by weight, preferably about 0.05 percent to about 3.0 percent by weight.

A buffering ingredient may also be added to the emulsion coating compositions of the invention in order to prevent natural degradation of the flavoring components. Generally, the Ph of these compositions is adjusted to 3.5 to about 7, preferably from about 5 to about 6. The buffering ingredients such as an alkali metal salt of a weak organic acid, for instance, sodium benzoate, sodium citrate, sodium phosphate, or potassium tartrate is generally added in an amount of about 0.1 to about 1.0 percent by weight.

In addition to the buffering ingredients, the compositions of the invention can optionally contain at least one humectant selected from the group consisting of glycerine, xylitol, sorbitol and propylene glycol. Generally, the liquid humectants are utilized in the proportion of about 3 percent to about 12 percent by weight based upon the total weight of the composition. Preferably, the liquid humectant is utilized in an amount of about 3 to 4 percent weight of the coating emulsion.

Solid humectants can be utilized at levels from about 1% by weight to about 50% by weight, thereby imparting a broad range of delivery, mouthfeel and taste properties.

More particularly, the chewing gums of the present invention comprise in the range of about 15% to about 60% by weight gum base. Several formulations are possible, depending upon the type of gum desired (i.e., sugar-containing or sugarless chewing gums, conventional stick gums, or bubble gums). Suitable raw materials for gum bases include chicle, latex, RBH resin, crown gum, Malsa compound PU-C, picolyte resin, candelilla wax, chiquibil gum, and the like.

Conventional chewing gum bases that may be obtained from commercial suppliers are generally suitable.

Suitable conventional stick gum bases (i.e., as opposed to bubble gum bases) include "Paloja"; "Firm Paloja"; "Berguna"; and "Dreyco," all available from the L.A. Dreyfus Corporation, P.O. Box 500, South Plainfield N.J., and "Synthetic Base No. 2939" and "Natural Base No. SC319," which can be obtained from the American Chicle Company, New York, N.Y.

In general, "Paloja," "NOVA" and "Dreyco" are preferred chewing gum bases.

Suitable bubble gum bases include: "D.C."; "Extra Soft"; "Oak"; "Grande"; "Soft Ideal"; "Ideal"; "Model"; and "Ladco," all available from the L.A. Dreyfus Corporation.

Other examples of such materials may be found in Vol. 30 of the U.S. Federal Register, No. 247, Sec. 121.1059, dated Dec. 23, 1965.

The gum base will also include a flavoring in an amount ranging from about 0.3 to about 1.5% by weight and preferably from about 0.8 to about 1.2% by weight of the final chewing gum product. The flavoring may comprise oils derived from plants, leaves, flowers, and the like. Representative flavor oils of this type include essential oils such as peppermint oil, spearmint oil, clove oil, bay oil, anise oil, eucalyptus oil, thyme oil, cedar leaf oil, cinnamon oil, oil of nutmeg, oil of sage, oil of bitter almonds, cassia oil, and methylsalicylate (oil of wintergreen), and also include citrus oils such as lemon oil, orange oil, lime oil, grapefruit oil, fruit essences such as apple essence, pear essence, peach essence, strawberry essence, apricot essence, raspberry essence, cherry essence, plum essence, pineapple essence, watermelon, banana and the like; bean-derived flavors, such as coffee, cocoa and the like; wine-derived flavors, such as curacao, and the like; and pungent materials, such as affinin, pepper, mustard and the like.

The sweetening agent ingredient used in the chewing gum bases of this invention may be selected from a wide range of materials, including water-soluble sweeteners, water-soluble artificial sweeteners, and dipeptide based sweeteners, including mixtures thereof. Without being limited to particular sweetening agents, representative illustrations encompass:

A. Water-soluble sweetener such as monosaccharides, disaccharides, and polysaccharides such as xylose, ribose, glucose, mannose, galactose, fructose, dextrose, sucrose, maltose, partially hydrolyzed starch or corn syrup solids and sugar alcohols such as sorbitol, xylitol, mannitol, hydrogenated glucose syrup and mixtures thereof, and B. Water-soluble artificial sweeteners such as the soluble saccharin salts, i.e., sodium or calcium saccharin salts, cyclamate salts, such as the sodium salt and the like, and the free acid form of saccharin; dipeptide based sweetening agents such as L-aspartyl-L-phenyl-alanine methyl ester and materials described in U.S. Pat. Nos. 3,492,131 and 3,642,491 and the like; dihydrochalcone; glycyrrhizin; *Stevia*

*rebaudiana* (Stevioside); and the synthetic sweetener 3,6-dihydro-6-methyl-1,2,3-oxathiazin-4-one-2,2-dioxide, particularly the potassium (Acesulfame-K), sodium and calcium salts thereof, as described in German Pat. No. 2,001,017.7.

The use of xylitol in various products such as chewing gums is reported in U.S. Pat. No. 3,296,079 to Griffin, issued Jan. 3, 1067; U.S. Pat. No. 3,655,866, issued to Bilotti on Apr. 11, 1972; U.S. Pat. No. 3,914,434 issued to Bohni on Oct. 21, 1975; U.S. Pat. No. 4,000,320 issued to Klose, et al on Dec. 28, 1976 and U.S. Pat. No. 3,899,593 issued to Hammond et al., on Aug. 12, 1975.

The effect of chewing gums containing xylitol and sorbitol on plaque formation is discussed in Caries Res. 17:569–378 (1983), and in JADA, Vol. 108, 587–592 (1984).

In those instances where the sweetening agent chosen provides more than bulk or texture, such as where the artificial sweeteners of Category B above are used, the term sweetening agent, for purposes of this invention, is meant to include artificial sweeteners and bulk sweeteners. Typical bulk sweeteners such as one or more sugar alcohols, including sorbitol, mannitol, xylitol and the like, or mixtures thereof, are utilized in amounts of about 20% to about 70%, preferably about 30% to about 60% by weight, together with one ore more of the artificial sweeteners described in Category B above, which artificial sweeteners are utilized in amounts of about 0.05% to about 0.3%, preferably about 0.18% to about 0.22%, by weight, all percentages being based on the weight of the total composition.

In a preferred embodiment of this invention, the sweetening agent used is a combination of an artificial sweetener such as sodium saccharin, and bulk sweeteners such as mannitol, sorbitol, and hydrogenated glucose syrup, generally in amounts of 0.05% to about 0.3%, preferably about 0.18% to about 0.22% artificial sweetener; about 2% to about 15%, preferably about 4% to about 8% mannitol; and about 20% to about 50%, preferably about 30% to about 40% sorbitol, and about 20% to about 50%, preferably about 30% to 40% hydrogenated glucose syrup with the total bulk sweetener content being from about 30% to about 60% depending upon the effect desired, all percentages being by weight, based on the weight of the total chewable tooth cleaning composition is preferred, the sweetening agent used in the practice of this invention may include sugar as well as an artificial sweetener.

The combination of artificial sweeteners and bulk sweeteners used in this invention generally provides approximately equivalent levels of bulk and sweetness as do the saccharide type of sweeteners in category A above. The amounts of sweetening agents described above are ordinarily necessary to achieve a desired level of sweetness independent of the flavor level achieved from the inclusion of flavoring agents.

Yet another desirable ingredient in the composition of the present invention is the use of glycerin. In the chewing gum aspect of the present invention glycerin serves to soften and maintain the chewability of the chewing gum for prolonged periods. The glycerin also adds to the sweetness of the composition. The glycerin is ordinarily added at levels of from about 0.2% to about 5% by weight of the composition.

Plasticizing-softening agents commonly used in the chewing gum compositions are suitable for use in the practice of this invention, including lanolin, propylene glycol, glycerol, acetylated monoglyceride, glyceryl triacetate, glyceryl diacetate, fatty acids, lecithin, glycerin, and the like and mixtures thereof. In a preferred embodiment, a combination of acetylated monoglyceride, lecithin and glycerin can be used, generally in amounts of about 0.5% to about 0.5% acetylated monoglyceride, about 0.1% to about 0.7% lecithin and about 2.0% to about 15.0% glycerin; preferably about 0.1% to about 0.3% acetylated monoglyceride, about 0.4% to about 0.6% lecithin and about 7.0% to about 9.0% glycerin, percents being by weight, based on the weight of the total chewable tooth cleaning compositions.

The coating process used with the chewing gums of the present invention allows the therapeutic emulsions to:

a. be applied to conventional chewing gum in a controlled means, b. be released at a substantially constant, therapeutically effective, dosage level from the chewing gum during chewing, c. be released at a substantially constant therapeutically effective release rate from the chewing gum during chewing, d. substantially avoid being entrapped and/or bound in the chewing gum base during chewing, e. be applied to conventional chewing gum while avoiding interfering with chewing gum manufacturing processes, and f. be applied to chewing gum without negatively effecting the hedonic properties of said gum.

A unique feature of the chewing gum coating process of the present invention is that the melt-emulsions can be applied to the chewing gum utilizing a variety of coating techniques including printing, film making, adhesive application and textile dyeing processes. Each of these coating applications can be used to deliver controlled quantities of melt emulsions to the surface of gum to achieve plaque disruption effects when these coated gums are chewed.

Each of the coatings obtained from these various applications can be laid down on the gum surface in a pattern and in color such that the coating per se' is distinctive from its chewing gum substrate. The patterns and designs useful for these coatings include stripes, cross hatch designs, random markings and the like, all of which effectively communicate the plaque fighting and other therapeutic attribute of the coated chewing gums.

Alternatively the coatings of the melt emulsions of the present invention can be made indistinguishable from the gum surface. This attribute is particularly important when the melt emulsion contains a therapeutic substance prescribed for treating a youngster and the parent does not wish to alarm the youngster that a medicine is being chewed.

Additionally, the melt-emulsion coatings of the present invention can be applied to the surface of the chewing gum as a raised, distinctive "rib" of active ingredients. Again these raised coatings serve as a signal to the consumer of the plaque fighting and/or other therapeutic attributes of the chewing gum.

The emulsion of polydimethyl siloxane in surfactant or emulsifier is obtained by heating the requisite quantity of surfactant and polydimethyl siloxane together in an oil bath controlled at between about 100° C. and about 170° C. As the surfactant or emulsifier melts, the mixture easily emulsifies with moderate stirring into a uniform "cream". This "cream" is beneficially emulsified into smaller emulsion particle size by use of conventional high shear mixing devices such as homomixers, high power-small orifice devices and the like.

Additional materials required can be blended into the melt-emulsion, again with moderate stirring. Due to the volatility of the various flavor oils that can be used, it may be desirable to cool the hot melt emulsion slightly while retaining fluidity before adding the flavor oils. Details of preparing these melt emulsions are described in the various examples below.

The chewing gum is prepared following accepted chewing gum processing as generally described in the various U.S. Patents referenced above. The chewing gum in sheet or slab form is cooled before the emulsion is applied to the chewing gum surface via the various coating processes of the present invention as described below.

Various embodiments of the invention can be employed to lay down a coming of the melt emulsion on the sheets of chewing gum. Such coating means generally do not interfere with the manufacturing and processing equipment used to manufacture sheets of chewing gum. Ideally, one or more of the chewing gum coating processes disclosed in the examples below can be retrofitted into most existing gum manufacturing equipment and processes.

The preferred coating processes used in the present invention are derivations of: printing, film making, adhesive coating and textile dyeing which until now have not been applied to the coating of heated melt emulsions to chewing gums.

The present invention will be further illustrated with reference to the following examples which will aid in the understanding of the present invention, but which are not to be construed as limitations thereof. All percentages reported herein, unless otherwise specified, are percent by weight. All temperatures are expressed in degrees Celsius.

EXAMPLE 1

Emulsions for use in coating the chewing gums of the invention are prepared as follows:

A. The ingestible nonionic surfactant, Pluronic F-127, 560 g, and polydimethyl siloxane, Dow Corning 360 Medical Fluid, 1000 CS. viscosity, 200 g, are heated to 150° C. with constant mixing using a lightning mixer. The heated emulsion is then transferred to a homomixer for 15 minutes, while the temperature is increased to 180° C.

The emulsion is cooled to 130° C. and the following is added with conventional mixing: insoluble saccharin, 1 g, peppermint oil, 0.2 g, and carrageenan powder, 30 g. This melt emulsion is poured onto a flat surface and cooled until solid. The solid emulsion is broken up into workable pieces or flaked using a doctor blade in a standard flaking operation. The flaked emulsion is stored until needed for preparing formulations as described in Tables I and II, and various examples below.

B. 200 g of the ingestible nonionic surfactant, Pluronic F-108, and 200 g of the polydimethyl siloxane, Dow Corning 360 Medical Fluid at 12,500 CS., are heated to 165° C. with constant overhead stirring using a lightning mixer. The mixture is transferred to a homomixer for 15 minutes. While the temperature is increased to 190° C. In a separate vessel, dry powdered sorbitol, 200 g, was melted and heated to 150° C. with mixing. The molten sorbitol was added to the homomixer containing the surfactant-polydimethyl siloxane emulsion and emulsified into said emulsion, forming a three phase melt emulsion. The three phase melt emulsion is mixed with a homomixer for 15 minutes.

The melt emulsion is either poured onto a flat surface for cooling, until solid or chilled and flaked on a cold roller flaker. The resulting solids can be stored until needed for remelting, with or without therapeutic additives such as described in Table II. These therapeutic substances are added to the emulsion using heating and mixing to effect uniform dispersion in the emulsion.

Examples 2 through 6 below describe various coating processes used to coat sheets of commercial chewing gum with the emulsions described in Examples 1A and 1B.

EXAMPLE 2

The solid, flaked emulsion described in Example 1A was melted at 130° C. and forced through a heated orifice of 0.010 inches diameter under constant pressure onto a mixing sheet of gum. Following the orifice was a distributor blade of such configuration that a uniform bead of the heated emulsion was coated onto the sheet of chewing gum in the shape of a stripe dependent upon the distributor blade configuration and pressure.

The resulting application provided a single striped surface coating of the emulsion of approximately 10 mg by weight (0.4% of gum weight).

Increasing the orifice to 0.020 inches produced a ½ inch stripe of emulsion coating on the chewing gum sheet, approximately 40 mg by weight. The control of: orifice size, pressure, speed of the moving sheet of gum and configuration of distributor blade produced a wide range of emulsion coatings on the chewing gum. The resulting stripes are flexible, do not separate from the gum when handled and upon chewing the various striped coatings are released from the gum at a controlled rate and in a controlled amount. The released coatings are immediately deposited on the teeth and mucosa imparting a slick, just-brushed feeling to the mouth, which historically is associated with delivery to the mouth of these emulsions: using other delivery systems such as sprays and dental floss.

EXAMPLE 3

The solid emulsion prepared according to Example 1B was melted at 110° C. and coated onto a embossing print roller at the same temperature and rolled across a sheet of chewing gum. The emulsion coating was transferred from the heated roller to the cool sheet of gum essentially in the configuration of the print roller. The embossed pattern of emulsion coating, upon cooling did not come off the gum when handled, Upon chewing, the coated gum sample was perceived as similar to the sample described in Example 2.

EXAMPLE 4

A Slidex WAXMASTER ™ adhesive coater Model 400 was filled with emulsions prepared according to Examples 1A and 1B, to which had been added a variety of flavors, sweeteners, mouth feel agents and therapeutic substances as described in Tables I and II. These various emulsions melted at 100° C. and were picked up by the coating roller at the same temperature. The quantity of each emulsion coating applied to the roller is controlled by a doctor blade fixed at varying distances from the roller.

As the gum sheet is moved past the coating roller by a second roller positioned immediately above the coating roller with a gap equal to or slightly less than the gum sheet thickness; the hot emulsion is transferred to the cool gum sheet at varying thicknesses ranging from between about 0.001 and about 0.006 inches. The emulsion is coated onto the gum surface with whatever pattern is on the surface of the coating roller.

This technique as well as the other examples herein provide for any desired mg quantity of the active ingredient on a wide range of piece size and shape, for example, from "mini's" to regular (about 2.5 g) sticks to bubble gum slabs (about 10 g).

EXAMPLE 5

Using the same apparatus described in Example 4, the doctor blade is notched with notches ranging from 0.001 to 0.010 inches in each location that a coating stripe is desired on the chewing gum surface. The remainder of the doctor blade makes clean contact with the coating roller so as to produce quantitative stripes of desired width and thickness. The resulting striped emulsion coated chewing gum samples are perceived to be similar to those described in Example 2 above.

EXAMPLE 6

Using the apparatus described in Example 4 where the coating roller is modified with grooves 0.002 to 0.010 inches deep by 0.125 inches wide with the remainder of the doctor blade making clean contact with the coating roller, produces a quantitative stripe of the desired width and thickness. The resulting striped coated emulsion chewing gum samples are similar to those described in Example 2.

EXAMPLE 7

Samples of a coated therapeutic chewing gum were prepared according to the process described in Example 4 where the emulsions contained from between about 1.2 and about 4.0% by weight microbially active stannous fluoride. The coated gums were chewed and were perceived to be similar to those described in Example 2 above.

The various coated chewing gums of the invention produced according to Examples 1–7 above were observed to release a substantial amount of the coating at the outset of chewing with a resultant therapeutic effect.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A therapeutic preparation effective in treating localized conditions of the mouth, teeth and gums, said conditions being selected from the group consisting of plaque, gingivitis, hypersensitivity, stomatitis and microbes in the mouth, said preparation being in the form of a chewing gum wherein:
    A. the chewing gum is coated with an emulsion comprising an ingestible surfactant-emulsifier and a polydimethyl siloxane insoluble in said surfactant-emulsifier,
    B. the emulsion is applied to the chewing gum by means of a coating process selected from the group of coating processes consisting of printing, film coating, adhesive applications and textile dyeing, and
    C. the emulsion coating on said gum is releasable during chewing, at a therapeutic effective rate and in a therapeutic effective amount.

2. The therapeutic preparation according to claim 1, wherein the emulsion coating comprises a therapeutic substance selected from the group consisting of antimicrobials, microbially active stannous fluoride, chlorhexidine, triclosan, zinc chloride, cationic antimicrobial agents, cetylpyridinium chloride, antioxidants, propyl gallate, enzymes, antibiotics, tetracycline, mineral salts, pectin, strontium chloride, potassium nitrate, metronidazole benzocaine, analgesics for mouth and throat discomfort, sanguinarine extract, stearoyl-2-lactate, cough and cold remedies, and remineralizing substances.

3. The therapeutic preparation according to claim 1, wherein said coating releases during chewing at an effective plaque disrupting rate and in an effective plaque disrupting amount.

4. The therapeutic preparation according to claim 2, wherein the emulsion coating comprises microbially active stannous fluoride, releasable at an effective antigingivitis rate and in an effective antigingivitis amount.

5. The therapeutic preparation according to claim 2, wherein the emulsion coating comprises microbially active stannous fluoride releasable at an effective hypersensitivity treatment rate and in an effective hypersensitivity treatment level.

6. The therapeutic preparation according to claim 2, wherein the emulsion coating comprises microbially active stannous fluoride releasable at an effective stomatitis treatment rate and at an effective stomatitis treatment level.

7. The therapeutic preparation according to claim 2, wherein the emulsion coating comprises chlorhexidine releasable at an effective gingivitis treatment rate and at an effective gingivitis treatment level.

8. The therapeutic preparation according to claim 2, wherein the emulsion coating comprises triclosan releasable at an effective gingivitis treatment rate and at an effective gingivitis treatment level.

9. The coated chewing gum according to claim 1, wherein the ingestible surfactant is selected from the group consisting of:
    sodium lauryl sulfate,
    sodium lauryl sarcosinate,
    polyethylene glycol stearate,
    polyethylene glycol monostearate,
    coconut monoglyceride sulfonates,
    block copolymers of polyoxyethylene and polyoxybutylene,
    alkylpolyglycol ether carboxylates,
    polyethylene derivatives of sorbitan esters,
    propoxylated cetyl alcohol,
    block copolymers comprising a congeneric mixture of conjugated polyoxybutylene and polyoxyethylene compounds having as a hydrophobe a polyoxybutylene polymer of at least 1200 molecular weight,
    a salt of a fatty acid (soap powder), and emulsified polyethylene glycols, polyethylene glycol oleate, polyethylene glycol beeswax and monomethyl ether polyethylene glycol.

10. The coated chewing gum according to claim 1, wherein the polydimethyl siloxane has the general structure:

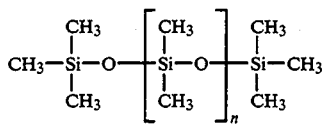

wherein n represents a whole number from between about 100 and 5,000, and the polydimethyl siloxane has a viscosity from between about 350 and about 12,500 centistokes.

11. A coated chewing gum according to claim 1, wherein the coating is applied to the chewing gum at from between about 0.5% and about 6% by weight of the gum, or from between about 10 mg/piece and about 100 mg/piece.

12. A coated chewing gum according to claim 9, wherein the ingestible surfactant is a polyoxyethylene-polyoxybutylene block copolymer.

13. A chewing gum according to claim 3, wherein the plaque disrupting, emulsion coating is applied to the chewing gum at an elevated temperature by means of a printing process.

14. A chewing gum according to claim 3, wherein the plaque disrupting, emulsion coating is applied to the chewing gum at an elevated temperature by means of a film coating process.

15. A chewing gum according to claim 3, wherein the plaque disrupting, melt-emulsion coating is applied to the chewing gum at an elevated temperature by means of an adhesive application process.

16. A chewing gum according to claim 3, wherein the plaque disrupting, emulsion coating is applied to the chewing gum at an elevated temperature by means of a textile dyeing process.

17. A method of manufacturing a therapeutic chewing gum comprising, preparing a sheet of chewing gum, coating said sheet of gum with an emulsion maintained at a temperature between about 100° C. and about 200° C., wherein:
   a. the emulsion comprises an ingestible surfactant or emulsifier and a polydimethyl siloxane insoluble in said surfactant or emulsifier, and
   b. the coating process is selected from the group of coating processes consisting of printing, film making, adhesive applications and textile dyeing.

* * * * *